(12) United States Patent
Cheong et al.

(10) Patent No.: US 12,397,011 B2
(45) Date of Patent: Aug. 26, 2025

(54) METHOD FOR PREVENTING OR TREATING CANCER USING SYT11 INHIBITOR

(71) Applicants: KOREA RESEARCH INSTITUTE OF BIOSCIENCE AND BIOTECHNOLOGY, Daejeon (KR); INDUSTRY-ACADEMIC COOPERATION FOUNDATION, YONSEI UNIVERSITY, Seoul (KR)

(72) Inventors: Jae Ho Cheong, Seoul (KR); Mi Sun Won, Daejeon (KR); Bo Kyung Kim, Daejeon (KR); Hyun Seung Ban, Daejeon (KR); Kyung Chan Park, Daejeon (KR); Young Il Yeom, Daejeon (KR)

(73) Assignees: KOREA RESEARCH INSTITUTE OF BIOSCIENCE AND BIOTECHNOLOGY, Daejeon (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 1022 days.

(21) Appl. No.: 17/234,455

(22) Filed: Apr. 19, 2021

(65) Prior Publication Data

US 2021/0361694 A1 Nov. 25, 2021

Related U.S. Application Data

(63) Continuation-in-part of application No. PCT/KR2019/013686, filed on Oct. 17, 2019.

(30) Foreign Application Priority Data

Oct. 19, 2018 (KR) ........................ 10-2018-0125073

(51) Int. Cl.
*A61K 31/7105* (2006.01)
*A61P 35/00* (2006.01)
(Continued)

(52) U.S. Cl.
CPC .......... *A61K 31/7105* (2013.01); *A61P 35/00* (2018.01); *C12N 15/1138* (2013.01);
(Continued)

(58) Field of Classification Search
CPC .............. A61K 31/7105; A61K 31/713; A61K 31/7088; A61K 39/3955; A61P 35/00;
(Continued)

(56) References Cited

U.S. PATENT DOCUMENTS 10,221,458 B2  3/2019 Lai
2008/0221056 A1  9/2008 Baylin et al.
(Continued)

FOREIGN PATENT DOCUMENTS

CN  104513851 A  4/2015
CN  107893078 A  * 4/2018  ........... C12N 15/113
(Continued)

OTHER PUBLICATIONS

Meta-Analysis of Gene Expression Signatures Defining the Epithelial to Mesenchymal Transition during Cancer Progression Christian J. Groger et al., PLOSOne, Dec. 2012 | vol. 7 | Issue 12 | e51136 (Year: 2012).*
(Continued)

*Primary Examiner* — Ram R Shukla
*Assistant Examiner* — Shabana S Meyering
(74) *Attorney, Agent, or Firm* — Hauptman Ham, LLP

(57) ABSTRACT

The present invention relates to a method for preventing or treating cancer comprising administering a Synaptotagmin 11 (SYT11) inhibitor to a subject, a method for diagnosing
(Continued)

cancer comprising measuring an expression level of SYT11, and a method for screening a preparation for treating cancer.

5 Claims, 10 Drawing Sheets

Specification includes a Sequence Listing.

(51) Int. Cl.
  *C12N 15/113* (2010.01)
  *C12Q 1/6886* (2018.01)
  *G01N 33/50* (2006.01)
  *G01N 33/574* (2006.01)

(52) U.S. Cl.
  CPC ..... *C12Q 1/6886* (2013.01); *G01N 33/57446* (2013.01); *G01N 33/57492* (2013.01); *C12N 2310/11* (2013.01); *C12N 2310/122* (2013.01); *C12N 2310/14* (2013.01); *C12N 2310/531* (2013.01); *C12Q 2600/106* (2013.01); *G01N 33/5011* (2013.01); *G01N 2500/10* (2013.01)

(58) Field of Classification Search
  CPC ............ C12N 15/1138; C12N 2310/11; C12N 2310/122; C12N 2310/14; C12N 2310/531; C12N 15/113; C12N 2310/315; C12N 2310/341; C12N 2310/346; C12N 2320/30; C12Q 1/6886; C12Q 2600/106; C12Q 2600/136; C12Q 2600/158; G01N 33/57446; G01N 33/57492; G01N 33/5011; G01N 2500/10; G01N 33/57484; G01N 2500/00
  See application file for complete search history.

(56) References Cited

U.S. PATENT DOCUMENTS

| | | | |
|---|---|---|---|
| 2009/0275633 | A1 | 11/2009 | Esteller |
| 2013/0260376 | A1* | 10/2013 | Gupta ................... C12Q 1/6886 435/6.13 |
| 2014/0031257 | A1 | 1/2014 | Lothe et al. |
| 2014/0206574 | A1 | 7/2014 | Chapman et al. |
| 2015/0361502 | A1 | 12/2015 | Lai |
| 2018/0031562 | A1 | 2/2018 | Llorente et al. |
| 2019/0024179 | A1 | 1/2019 | Kanda |
| 2019/0136330 | A1 | 5/2019 | Lai |

FOREIGN PATENT DOCUMENTS

| | | |
|---|---|---|
| CN | 108165631 A | 6/2018 |
| KR | 10-2014-0057361 A | 5/2014 |
| KR | 10-2015-0067151 A | 6/2015 |
| WO | 2016/143697 A1 | 9/2016 |
| WO | 2016/181979 A1 | 11/2016 |
| WO | 2016-201064 A1 | 12/2016 |
| WO | 2017-176630 A1 | 10/2017 |

OTHER PUBLICATIONS

Role of epithelial-mesenchymal transition in gastric cancer initiation and progression, Zhao Peng et al., World J Gastroenterol May 14, 2014; 20(18): 5403-5410 ISSN 1007-9327 (print) ISSN 2219-2840 (online) (Year: 2014).*
English translation of CN-107893078-A marked as CN-107893078-MT (Year: 2018).*
Choi JD, Lee JS. Interplay between Epigenetics and Genetics in Cancer. Genomics Inform. Dec. 2013;11(4):164-73. doi: 10.5808/GI.2013.11.4.164. Epub Dec. 31, 2013. PMID: 24465226; PMCID: PMC3897842 (Year: 2013).*
Cheung VG, et al., Natural variation in human gene expression assessed in lymphoblastoid cells. Nat Genet. Mar. 2003;33(3):422-5. doi: 10.1038/ng1094. Epub Feb. 3, 2003. PMID: 12567189 (Year: 2003).*
International Search Report dated Jan. 20, 2020, in connection with corresponding International Patent Application No. PCT/KR2019/013686, citing the above references.
PCT Written Opinion dated Jan. 17, 2020, in connection with corresponding International Patent Application No. PCT/KR2019/013686, citing the above references.
Hao Jin et al., "Synaptotagmin-7 is overexpressed in hepatocellular carcinoma and regulates hepatocellular carcinoma cell proliferation via Chk1-p53 signaling," OncoTargets and Therapy, 2017, vol. 10, pp. 4283-4293.
Maria Vias et al., "Pro-neural transcription factors as cancer markers," BMC Medical Genomics, 2008, pp. 1-16.
Kanda M et al., "Discovery of synaptotagmin 7 as a driver of liver metastasis formation of gastric cancer", Oncogene, 2018.
Kanda M et al., "Synaptotagmin Xlll expression and peritoneal metastasis in gastric cancer", BJS, 2018; vol. 105, pp. 1349-1358.
J Jonklaas et al., "Novel biomarker SYT12 may contribute to predicting papillary thyroid cancer outcomes", Future Science OA (2018), vol. 4, No. 1, FSO249, Cited in NPL No. 1.
Kewei Wang et al., "Synaptotagmin7 Is Overexpressed In Colorectal Cancer And Regulates Colorectal Cancer Cell Proliferation", Journal of Cancer, 2018, vol. 9, No. 13, pp. 2349-2356.
Chika Saegusa et al., "Synaptotagmin V Is Targeted to Dense-core Vesicles That Undergo Calcium-dependent Exocytosis in PC12 Cells", The Journal of Biological Chemistry, 2002. Volume 277, No. 27, p. 24499-24505.
Molly Craxton, "Synaptotagmin gene content of the sequenced genomes", BMC Genomics, 2004, vol. 5, No. 43, pp. 1-14.
Razvan Cristescu et al., "Molecular analysis of gastric cancer identifies subtypes associated with distinct clinical outcomes", Nature Medicine, 2015, pp. 1-10, Cited in Specification.
Extended European Search Reports (EESR) issued on Nov. 24, 2021, for the corresponding European Patent Application No. 19873496.4.
H. Yeo et al. "Developmental expression and subcellular distribution of synaptotagmin 11 in rat hippocampus," Neuroscience, vol. 225, Aug. 6, 2012, pp. 35-43; Cited in NPL No. 1.
The Japanese Gastric Cancer Association general meeting report, vol. 89, 2017, p. 256, cited in NPL No. 3.
Paula Jimenez Fonseca et al., "Lauren subtypes of advanced gastric cancer influence survival and response to chemotherapy: real-world data from the AGAMENON National Cancer Registry", British Journal of Cancer, 2017, vol. 117, pp. 775-782, cited in NPL No. 3.
Japanese Office Action issued on Jul. 22, 2024, in connection with the Japanese Patent Application No. 2021-521300 with its English translation, 10 pages.

* cited by examiner

SEQUENCE LISTING

```
<160> NUMBER OF SEQ ID NOS: 20

<210> SEQ ID NO 1
<211> LENGTH: 431
<212> TYPE: PRT
<213> ORGANISM: Homo sapiens

<400> SEQUENCE: 1

Met Ala Glu Ile Thr Asn Ile Arg Pro Ser Phe Asp Val Ser Pro Val
1               5                   10                  15

Val Ala Gly Leu Ile Gly Ala Ser Val Leu Val Val Cys Val Ser Val
            20                  25                  30

Thr Val Phe Val Trp Ser Cys Cys His Gln Gln Ala Glu Lys Lys Gln
        35                  40                  45

Lys Asn Pro Pro Tyr Lys Phe Ile His Met Leu Lys Gly Ile Ser Ile
    50                  55                  60

Tyr Pro Glu Thr Leu Ser Asn Lys Lys Ile Ile Lys Val Arg Arg
65                  70                  75                  80

Asp Lys Asp Gly Pro Gly Arg Glu Gly Gly Arg Arg Asn Leu Leu Val
                85                  90                  95

Asp Ala Ala Glu Ala Gly Leu Leu Ser Arg Asp Lys Asp Pro Arg Gly
            100                 105                 110

Pro Ser Ser Gly Ser Cys Ile Asp Gln Leu Pro Ile Lys Met Asp Tyr
        115                 120                 125
```

-continued

Gly Glu Glu Leu Arg Ser Pro Ile Thr Ser Leu Thr Pro Gly Glu Ser
        130                 135                 140

Lys Thr Thr Ser Pro Ser Ser Pro Glu Glu Asp Val Met Leu Gly Ser
145                 150                 155                 160

Leu Thr Phe Ser Val Asp Tyr Asn Phe Pro Lys Lys Ala Leu Val Val
                165                 170                 175

Thr Ile Gln Glu Ala His Gly Leu Pro Val Met Asp Asp Gln Thr Gln
            180                 185                 190

Gly Ser Asp Pro Tyr Ile Lys Met Thr Ile Leu Pro Asp Lys Arg His
        195                 200                 205

Arg Val Lys Thr Arg Val Leu Arg Lys Thr Leu Asp Pro Val Phe Asp
210                 215                 220

Glu Thr Phe Thr Phe Tyr Gly Ile Pro Tyr Ser Gln Leu Gln Asp Leu
225                 230                 235                 240

Val Leu His Phe Leu Val Leu Ser Phe Asp Arg Phe Ser Arg Asp Asp
                245                 250                 255

Val Ile Gly Glu Val Met Val Pro Leu Ala Gly Val Asp Pro Ser Thr
            260                 265                 270

Gly Lys Val Gln Leu Thr Arg Asp Ile Ile Lys Arg Asn Ile Gln Lys
        275                 280                 285

Cys Ile Ser Arg Gly Glu Leu Gln Val Ser Leu Ser Tyr Gln Pro Val
290                 295                 300

Ala Gln Arg Met Thr Val Val Leu Lys Ala Arg His Leu Pro Lys
305                 310                 315                 320

Met Asp Ile Thr Gly Leu Ser Gly Asn Pro Tyr Val Lys Val Asn Val
                325                 330                 335

Tyr Tyr Gly Arg Lys Arg Ile Ala Lys Lys Thr His Val Lys Lys
            340                 345                 350

Cys Thr Leu Asn Pro Ile Phe Asn Glu Ser Phe Ile Tyr Asp Ile Pro
        355                 360                 365

Thr Asp Leu Leu Pro Asp Ile Ser Ile Glu Phe Leu Val Ile Asp Phe
370                 375                 380

Asp Arg Thr Thr Lys Asn Glu Val Val Gly Arg Leu Ile Leu Gly Ala
385                 390                 395                 400

His Ser Val Thr Ala Ser Gly Ala Glu His Trp Arg Glu Val Cys Glu
                405                 410                 415

Ser Pro Arg Lys Pro Val Ala Lys Trp His Ser Leu Ser Glu Tyr
            420                 425                 430

<210> SEQ ID NO 2
<211> LENGTH: 21
<212> TYPE: RNA
<213> ORGANISM: Artificial Sequence
<220> FEATURE:
<223> OTHER INFORMATION: Synthesized

<400> SEQUENCE: 2
caucaaagug cggagagaca a            21

<210> SEQ ID NO 3
<211> LENGTH: 19
<212> TYPE: RNA
<213> ORGANISM: Artificial Sequence
<220> FEATURE:
<223> OTHER INFORMATION: Synthesized

<400> SEQUENCE: 3
ccugcuaagc cgagacaaa                                                          19

<210> SEQ ID NO 4
<211> LENGTH: 19
<212> TYPE: RNA
<213> ORGANISM: Artificial Sequence
<220> FEATURE:
<223> OTHER INFORMATION: Synthesized

<400> SEQUENCE: 4
ccaggugucu cugucauau                                                          19

<210> SEQ ID NO 5
<211> LENGTH: 19
<212> TYPE: RNA
<213> ORGANISM: Artificial Sequence
<220> FEATURE:
<223> OTHER INFORMATION: Synthesized

<400> SEQUENCE: 5
gcagaaagcg cauugccaa                                                          19

<210> SEQ ID NO 6
<211> LENGTH: 57
<212> TYPE: DNA
<213> ORGANISM: Artificial Sequence
<220> FEATURE:
<223> OTHER INFORMATION: Synthesized

<400> SEQUENCE: 6
ccggcatcaa agtgcggaga gacaactcga gttgtctctc cgcactttga tgttttt              57

<210> SEQ ID NO 7
<211> LENGTH: 20
<212> TYPE: DNA
<213> ORGANISM: Artificial Sequence
<220> FEATURE:
<223> OTHER INFORMATION: Synthesized

<400> SEQUENCE: 7
ccggtctctc aggtaatcct                                                         20

<210> SEQ ID NO 8
<211> LENGTH: 20
<212> TYPE: DNA
<213> ORGANISM: Artificial Sequence
<220> FEATURE:
<223> OTHER INFORMATION: Synthesized

<400> SEQUENCE: 8
ctcattcttg gtggtgcgat                                                         20

<210> SEQ ID NO 9
<211> LENGTH: 20
<212> TYPE: DNA
<213> ORGANISM: Artificial Sequence
<220> FEATURE:
<223> OTHER INFORMATION: Synthesized

<400> SEQUENCE: 9
catcgtggct aaacaggtac                                                         20

<210> SEQ ID NO 10

```
<211> LENGTH: 19
<212> TYPE: DNA
<213> ORGANISM: Artificial Sequence
<220> FEATURE:
<223> OTHER INFORMATION: Synthesized

<400> SEQUENCE: 10
gcacgacctt gagggcagc                                                19

<210> SEQ ID NO 11
<211> LENGTH: 19
<212> TYPE: RNA
<213> ORGANISM: Artificial Sequence
<220> FEATURE:
<223> OTHER INFORMATION: Synthesized

<400> SEQUENCE: 11
ccuacgccac caauuucgu                                                19

<210> SEQ ID NO 12
<211> LENGTH: 57
<212> TYPE: DNA
<213> ORGANISM: Artificial Sequence
<220> FEATURE:
<223> OTHER INFORMATION: Synthesized

<400> SEQUENCE: 12
ccggcaacaa gatgaagagc accaactcga gttggtgctc ttcatcttgt tgttttt      57

<210> SEQ ID NO 13
<211> LENGTH: 19
<212> TYPE: RNA
<213> ORGANISM: Artificial Sequence
<220> FEATURE:
<223> OTHER INFORMATION: Synthesized

<400> SEQUENCE: 13
cagguuuugu gucaguacu                                                19

<210> SEQ ID NO 14
<211> LENGTH: 19
<212> TYPE: RNA
<213> ORGANISM: Artificial Sequence
<220> FEATURE:
<223> OTHER INFORMATION: Synthesized

<400> SEQUENCE: 14
acguuccuug uaaauccaa                                                19

<210> SEQ ID NO 15
<211> LENGTH: 49
<212> TYPE: DNA
<213> ORGANISM: Artificial Sequence
<220> FEATURE:
<223> OTHER INFORMATION: Synthesized

<400> SEQUENCE: 15
cctgctaagc cgagacaaac tcgagtttgt ctcggcttag caggttttt               49

<210> SEQ ID NO 16
<211> LENGTH: 49
<212> TYPE: DNA
<213> ORGANISM: Artificial Sequence
<220> FEATURE:
<223> OTHER INFORMATION: Synthesized
```

```
<400> SEQUENCE: 16
ccaggtgtct ctgtcatatc tcgagatatg acagagacac ctggttttt                49

<210> SEQ ID NO 17
<211> LENGTH: 49
<212> TYPE: DNA
<213> ORGANISM: Artificial Sequence
<220> FEATURE:
<223> OTHER INFORMATION: Synthesized

<400> SEQUENCE: 17
gcagaaagcg cattgccaac tcgagttggc aatgcgcttt ctgctttt                 49

<210> SEQ ID NO 18
<211> LENGTH: 19
<212> TYPE: DNA
<213> ORGANISM: Artificial Sequence
<220> FEATURE:
<223> OTHER INFORMATION: Synthesized

<400> SEQUENCE: 18
auatgacaga gacacctgg                                                 19

<210> SEQ ID NO 19
<211> LENGTH: 19
<212> TYPE: DNA
<213> ORGANISM: Artificial Sequence
<220> FEATURE:
<223> OTHER INFORMATION: Synthesized

<400> SEQUENCE: 19
uuggcaatgc gctttctgc                                                 19

<210> SEQ ID NO 20
<211> LENGTH: 19
<212> TYPE: DNA
<213> ORGANISM: Artificial Sequence
<220> FEATURE:
<223> OTHER INFORMATION: Synthesized

<400> SEQUENCE: 20
cctacgccac caatttcgu                                                 19
```

METHOD FOR PREVENTING OR TREATING CANCER USING SYT11 INHIBITOR

TECHNICAL FIELD

This application claims the priority of Korean Patent Application No. 10-2018-0125073, filed on Oct. 19, 2018, the entirety of which is a reference of the present application.

The present invention relates to a method for preventing or treating cancer, a method for diagnosing cancer, and a method for screening of preparation for treating cancer.

INCORPORATION BY REFERENCE

The sequence listing provided in the file entitled F-3_5900-0029_Substitute_Squence_Listing_CRF.txt, which is an ASCII text file that was created on Aug. 13, 2021, and which comprises 7,607 bytes, is hereby incorporated by reference in its entirety.

BACKGROUND ART

Cancer has a high death rate worldwide and is the most common death cause next to cardiovascular disease in the Western society. In particular, due to the aging of the population, the generalization of intake of high-fat diet due to westernization of dietary life, a rapid increase in environmental pollutants, an increase in volume of drink, and the like, colon cancer, breast cancer, prostate cancer, etc. are continuously increasing. In this situation, the creation of anticancer substances has been urgently required by enabling the early prevention and treatment of cancer to enhance human health, improve the quality of health life, and contribute to human health care promotion.

Among the cancers, gastric cancer has a high occurrence frequency and becomes a main cause of cancer-related deaths, especially in Asia. In Korea, 16.2% of cancer patients (20.3% of male cancer patients and 11.2% of female cancer patients) are estimated as gastric cancer patients. The symptoms of gastric cancer exhibit various aspects, from a case where there are no symptoms to severe pains, show general digestive symptoms without having any characteristic, and have almost no symptom in the early stage of gastric cancer. Even if there is the symptom, since the symptom is a relatively minor and has the degree to feel some digestive defects or abdominal uncomfortable, most people ignore the symptom to cause an increase in death rate of gastric cancer.

Various criteria are known for the classification of gastric cancer tissues. For example, types of gastric cancer may be classified through Lauren Classification. According to Lauren classification, anocarcinoma that occupies most of gastric cancer is classified into an intestinal type and a diffuse type. In the case of atrophic gastritis in which the infection of *Helicobacter pylori* has been lasted for a long time, especially intestinal-type gastric cancer occurs well, which forms ulcers well and forms a distinctive tubular structure with adhesive tumor cells gathered. On the other hand, the diffuse type is a type in which individual cells are infiltrated without the formation of clear mass due to the adhesion of tumor cells, and there is a problem that the diffuse type frequently occurs in young people and there is not a good prognosis. Many of patients with the diffuse-type gastric cancer are patients who are infected with *Helicobacter pylori* for the first time after being an adult, resulting in progressing to the diffuse-type gastric cancer due to the strong rejection of hosts. The response is excessively exhibited in young women with less atrophic gastritis, and eventually, the acute infection is not eliminated and edematous and nodular changes of the gastric mucosa are continued to progress to the diffuse-type gastric cancer with a very poor prognosis. Therefore, even in the same gastric cancer patients, young adults diagnosed as the diffuse-type gastric cancer are unlikely to be cured and eventually die within a few years. As described above, the diffuse-type gastric cancer is clinically difficult to be quickly identified, and as a result, the actual therapy is delayed or there is no therapeutic agent that has sufficient therapeutic effect even if the treatment is performed, and thus, the problem is continuing.

Recently, it was confirmed that in microarray analysis of tissues of gastric cancer patients, molecular subtypes may be classified into intestinal, stem-like, mixed stromal, and inflammatory subtypes according to an expression pattern characteristic of genes. As described above, the intestinal subtype is known as gastric cancer, which is easily treated as compared with the stem-like, mixed stromal, and inflammatory subtypes, and the stem-like subtype is reported to be hardly treated and belong to a gastric cancer group with a very bad prognosis. [Nature Medicine 2015; 21:449-456 Molecular analysis of gastric cancer identifies subtypes associated with distinct clinical outcomes]

In such a background, there is an urgent need for research and development of new technologies that can quickly diagnose and treat a specific cancer, which is hardly diagnosed.

DISCLOSURE

Technical Problem

Therefore, the present inventors have made many efforts to develop an anti-cancer agent that may exhibit an excellent effect on the treatment of cancer without causing side effects on the human body, and as a result, found that a SYT11 expression inhibitor had an excellent effect on the treatment of cancer within a range without toxicity and may be usefully used even for diagnosis, and then completed the present invention.

An object of the present invention is to provide a method for preventing or treating cancer comprising administering an expression inhibitor of Synaptotagmin 11 (SYT11) to a subject.

Another object of the present invention is to provide a pharmaceutical composition for preventing or treating cancer comprising an expression inhibitor of Synaptotagmin 11 (SYT11) as an active ingredient.

Yet another object of the present invention is to provide a use for preventing or treating cancer comprising administering a composition comprising an expression inhibitor of Synaptotagmin 11 (SYT11) to a subject.

Still another object of the present invention is to provide a method for diagnosing cancer comprising the steps of: (a) measuring an expression level of Synaptotagmin 11 (SYT11) from an isolated biological tissue sample; (b) comparing the expression level with an expression level of SYT11 of a normal control sample; and (c) determining the cancer when the expression level of SYT11 of the biological tissue sample is higher than the expression level of SYT11 of the normal control sample.

Still yet another object of the present invention is to provide a composition for diagnosing cancer comprising a preparation for measuring an expression level of Synaptotagmin 11 (SYT11).

Still yet another object of the present invention is to provide a method for screening a preparation for treating cancer comprising the steps of: (a) treating a candidate substance for treating cancer to isolated cancer cells expressing Synaptotagmin 11 (SYT11); (b) measuring an expression level of SYT11 in the isolated cancer cells treated with the candidate substance; and (c) determining the candidate substance to be used as a preparation for treating cancer when the expression level of SYT11 measured in step (b) is lower than that of isolated cancer cells non-treated with the candidate substance.

Technical Solution

In order to achieve the objects, an aspect of the present invention provides a method for preventing or treating cancer comprising administering an expression inhibitor of Synaptotagmin 11 (SYT11) to a subject.

Another aspect of the present invention provides a pharmaceutical composition for preventing or treating cancer comprising an expression inhibitor of Synaptotagmin 11 (SYT11) as an active ingredient.

Yet another aspect of the present invention provides a use for preventing or treating cancer comprising administering an expression inhibitor of Synaptotagmin 11 (SYT11) to a subject.

Still another aspect of the present invention provides a method for diagnosing cancer comprising the steps of: (a) measuring an expression level of Synaptotagmin 11 (SYT11) from an isolated biological tissue sample; (b) comparing the expression level with an expression level of SYT11 of a normal control sample; and (c) determining the cancer when the expression level of SYT11 of the isolated biological tissue sample is higher than the expression level of SYT11 of the normal control sample.

Still yet another aspect of the present invention provides a composition for diagnosing cancer comprising a preparation for measuring an expression level of Synaptotagmin 11 (SYT11).

Still yet another aspect of the present invention provides a method for screening a preparation for treating cancer comprising the steps of: (a) treating a candidate substance for treating cancer to isolated cancer cells expressing Synaptotagmin 11 (SYT11); (b) measuring an expression level of SYT11 in the isolated cancer cells treated with the candidate substance; and (c) determining the candidate substance to be used as a preparation for treating cancer when the expression level of SYT11 measured in step (b) is lower than that of isolated cancer cells non-treated with the candidate substance.

Advantageous Effects

According to the present invention, the method for preventing or treating the cancer comprising the SYT11 inhibitor to the subject has an excellent effect of inhibiting metastasis of cancer and preventing or treating cancer, by inhibiting migration and invasion of cancer cells, inhibiting the ability to adhere to the extracellular matrix, inhibiting secretion of various cancer metastasis-related cytokines, and inhibiting the proliferation of cancer cells.

In addition, in the present invention, since the correlation between the expression of SYT11 and the cancer was confirmed, there is an excellent effect in diagnosing cancer by measuring the expression level of SYT11.

MODES FOR THE INVENTION

Figure 1:
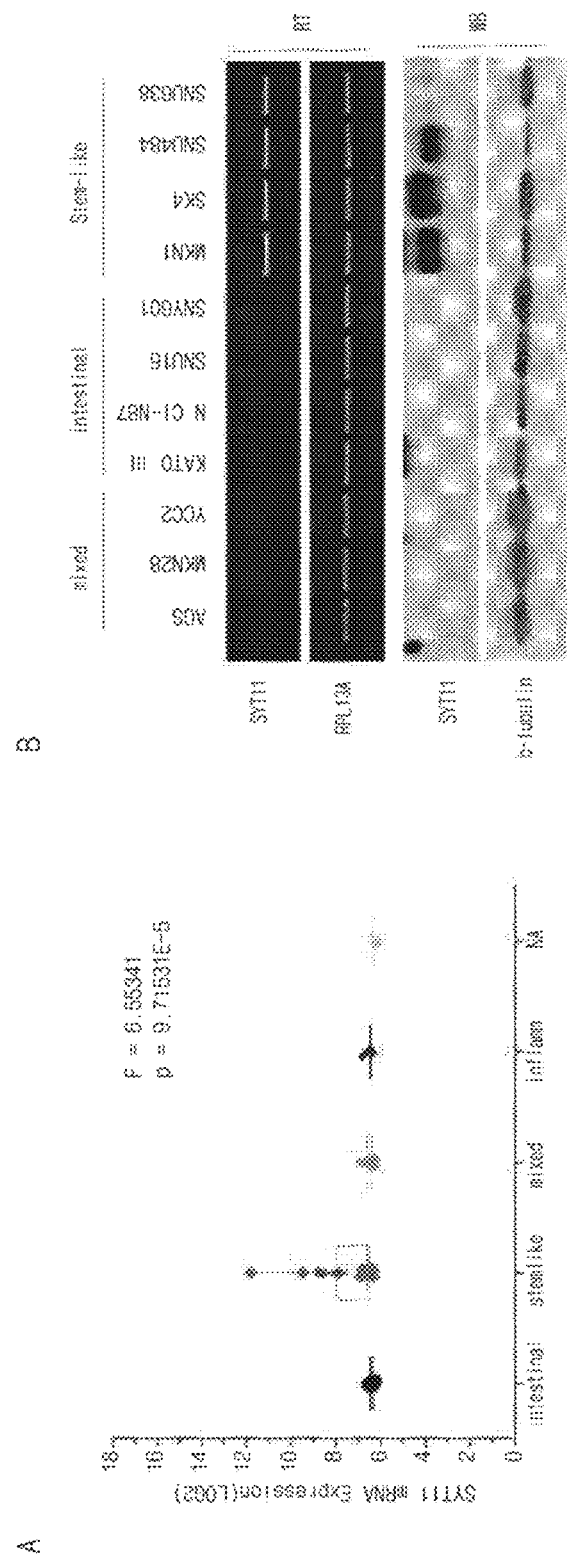
FIG. 1 is a diagram illustrating a result of confirming the enhancement of SYT11 expression in a stem-like subtype gastric cancer cell line among gastric cancer cell lines with intestinal, stem-like, mixed, and inflammatory subtypes.

An aspect of the present invention for achieving the object is to provide a method for preventing or treating cancer comprising administering a Synaptotagmin 11 (SYT11) inhibitor to a subject.

In the present invention, the term "SYT11 (Synaptotagmin 11, NM_152280.4)" is one of synaptotagmin gene families, encodes a protein similar to other family members known as calcium sensors, and adjusts the calcium-dependent modulation of membrane transport in synaptic transmission. The encoded protein is known as a matrix of Ubiquitin-E3-ligase parkin. The SYT11 has an amino acid sequence of SEQ ID NO: 1.

In a specific embodiment of the present invention, it was confirmed that the growth of cancer cells was suppressed when the expression of SYT11 was inhibited in human gastric cancer cell lines, lung cancer cell lines, colon cancer cell lines, liver cancer cell lines, and pancreatic cancer cell lines.

In another specific embodiment of the present invention, through human gastric cancer cell line analysis, molecular subtypes of a cancer cell line are classified into intestinal, stem-like, mixed, and inflammatory subtypes, and it was confirmed that in the stem-like subtype of the classified human gastric cancer cell line, the expression of SYT11 was increased.

In another specific embodiment of the present invention, in order to confirm the correlation with changes in metastasis of cells, that is, changes in migration and invasion abilities of cells by inhibiting SYT11 expression, when SYT11 was inhibited in gastric cancer cells, it was confirmed that the invasion and migration abilities were significantly reduced.

In yet another specific embodiment of the present invention, in order to confirm the correlation with a change in the ability to adhere to the extracellular matrix of cancer cells by inhibiting the SYT11 expression, when the expression of SYT11 was inhibited in gastric cancer cells, it was confirmed that the ability to adhere to the extracellular matrix was significantly reduced.

In yet another specific embodiment of the present invention, in order to confirm the correlation with a change in cancer cell metastasis-related growth factors or cytokines by inhibiting the SYT11 expression, when the expression of SYT11 was inhibited in gastric cancer cells, it was confirmed that cancer cell metastasis-related PDGF-AA, VEGF, HGF, IGFBP-2, IL-17A, IL-8, angiopoietin-1, angiopoietin-2, etc. were reduced.

In yet another specific embodiment of the present invention, it was confirmed that the tumors were reduced by the inhibition of the SYT11 expression in a mouse animal model.

In yet another specific embodiment of the present invention, it was confirmed that the proliferation of tumor cells was inhibited by the inhibition of SYT11.

In the present invention, the term "SYT11 inhibitor" is used in the meaning of collectively referring to all preparations of reducing the expression or activity of SYT11. Specifically, the SYT11 inhibitor may include all preparations of reducing the activity of SYT11 by reducing an expression level of SYT11 in a transcription, mRNA or translation level or inhibiting the activity of SYT11 by a method such as affecting the reduction of the expression of SYT11, directly acting on SYT11, or indirectly acting on a ligand thereof.

The SYT11 inhibitor is able to be used without limitation in the form thereof, such as compounds, nucleic acids, peptides, virus, vectors containing the nucleic acids, or the like capable of inhibiting the expression of SYT11 or the activity by targeting SYT11. The SYT11 inhibitor is not limited thereto, but there are miRNA, siRNA or shRNA that hydrolyzes mRNA of an SYT11 gene, and antisense oligonucleotide that reduces the expression of an SYT11 protein. Further, a SYT11 inhibitor that binds to the SYT11 protein to inhibit the function may include an aptamer or a low molecular compound.

In an exemplary embodiment, the siRNA may have a nucleotide sequence selected from SEQ ID NOS: 2, 3, 4, and 5.

TABLE 1

| SEQ ID NO: | siRNA sequence information |
|---|---|
| SEQ ID NO: 2 | 5'- CAU CAA AGU GCG GAG AGA CAA (dTdT) -3' |
| SEQ ID NO: 3 | 5'- CCU GCU AAG CCG AGA CAA A (dTdT) -3' |
| SEQ ID NO: 4 | 5'- CCA GGU GUC UCU GUC AUA U (dTdT) -3' |
| SEQ ID NO: 5 | 5'- GCA GAA AGC GCA UUG CCA A (dTdT) -3' |

In an exemplary embodiment, the shRNA may be shRNA having a nucleotide sequence selected from SEQ ID NOS: 6, 15, 16 and 17, and may be synthesized or modified shRNA, such as homologues, allogenic types, variants, derivatives, and fragments thereof. For example, a loop sequence (an underline of the following Table 2) existing at the center in the nucleotide sequence selected from SEQ ID NOS: 6 and 15 to 17 may be modified.

TABLE 2

| Sequence information | shRNA sequence information |
|---|---|
| SEQ ID NO: 6 | CCGGCATCAA AGTGCGGAGA GACAACTCGA GTTGTCTCTC CGCACTTTGA TGTTTTT |
| SEQ ID NO: 15 | CCTGCTAAGCCGAGACAAACTCGAGTTTGTCTCGG CTTAGCAGGTTTTT |
| SEQ ID NO: 16 | CCAGGTGTCTCTGTCATATCTCGAGATATGACAGA GACACCTGGTTTTT |
| SEQ ID NO: 17 | GCAGAAAGCGCATTGCCAACTCGAGTTGGCAATGC GCTTTCTGCTTTTT |

In an exemplary embodiment, the antisense oligonucleotide may be one or more antisense oligonucleotides selected from SEQ ID NOS: 18 and 19, and derivatives thereof. The derivatives may have phosphorothiotate modification and/or 2'-O-methylation modification in the one or more antisense oligonucleotides selected from SEQ ID NOS: 18 and 19.

TABLE 3

| Sequence information | Antisense oligonucleotide information | Description |
|---|---|---|
| AS-SYT11 (SEQ ID NO: 18) | 5'- mA*mU*A* T*G*A* C*A*G* A*G*A* C*A*C* C*TmG* mG-3' | 19mer, *: P = S, m: 2-o-methyl |
| AS-SYT11 (SEQ ID NO: 19) | 5'- mU*mU*G* G*C*A* A*T*G* C*G*C* T*T*T* C*T*mG* mC-3' | 19mer, *: P = S, m: 2-o-methyl |

In the present invention, the term "treatment" refers to clinically intervening to change a natural process of individuals or cells to be treated, which may be performed while a clinical pathological state is in progress or to prevent this state. The desired treating effect includes preventing occurrence or recurrence of disease, mitigating symptoms, reducing all direct or indirect pathological results according to disease, preventing metastasis, reducing a disease progressing rate, reducing or temporarily alleviating a disease condition, and exhibiting remission or improving a prognosis. Preferably, in the present invention, the treatment includes all actions that improve the progression of gastric cancer with administration of the composition comprising the substance of inhibiting SYT11. In addition, the "prevention" refers to all actions that inhibit or delay the onset of the gastric cancer with administration of the composition comprising the substance of inhibiting SYT11 according to the present invention.

In the present invention, the term "antisense oligonucleotide" is DNA, RNA, or derivatives thereof containing a nucleic acid sequence complementary to a sequence of specific mRNA and serves to inhibit the translation to a protein of mRNA by binding to the complementary sequence in mRNA. The antisense oligonucleotide sequence refers to a DNA or RNA sequence that may be complementary to the SYT11 mRNA and bind to the mRNA. The antisense oligonucleotide may inhibit the essential activity for translation of the SYT11 mRNA, translocation into the cytoplasm, maturation, maturation, or all other overall biological functions. The length of the antisense oligonucleotide may be 6 to 100 bases, preferably 8 to 60 bases, more preferably 10 to 40 bases. The antisense oligonucleotide may be synthesized in vitro in a conventional method to be administered in vivo or may be synthesized in vivo. One example of synthesizing the antisense oligonucleotide in vitro is to use RNA polymerase I. One example of synthesizing the antisense RNA in vivo allows the antisense RNA to be transcribed by using a vector having the origin of a multicloning site (MCS) in an opposite direction. The antisense RNA is preferably not translated into a peptide sequence so that a translation stop codon is present in the sequence. A design of the antisense oligonucleotide that may be used in the present invention may be made according to a method known in the art with reference to the nucleotide sequence of SYT11.

Specifically, the antisense oligonucleotide of the present invention may be oligonucleotide of SEQ ID NOS: 18 or 19 but is not limited thereto.

In addition, the oligonucleotide of SEQ ID NOS: 18 or 19 includes oligonucleotide and derivatives thereof comprising substantially the same nucleotide sequence as the oligonucleotide of SEQ ID NOS: 18 or 19. The oligonucleotide comprising substantially the same nucleotide sequence refers to oligonucleotide comprising a nucleotide sequence having sequence homology of 75% or more, 80% or more, 90% or more, and 95% or more with the nucleotide sequence of SEQ ID NOS: 18 or 19, respectively. The derivative may have phosphorothioate modification and/or 2'-o-methylation modification in one or more oligonucleotides selected from SEQ ID NOS: 18 and 19 but is not limited thereto.

In the present invention, the term "aptamer" as a single-stranded oligonucleotide refers to a nucleic acid molecule having a size of about 20 to 60 nucleotides and a binding activity to a predetermined target molecule. The aptamer may have various 3D structures according to a sequence and may have high affinity with a specific substance, like antigen-antibody reaction. The aptamer may inhibit the activity of the predetermined target molecule by binding to the predetermined target molecule. The aptamer of the present invention may be RNA, DNA, modified nucleic acid, or mixtures thereof, and may also be in a linear or cyclic form. Preferably, the aptamer may serve to inhibit the activity of SYT11 by binding to SYT11. Such an aptamer may be prepared from the sequence of SYT11 by a method known in the art.

In the present invention, the terms "miRNA," "siRNA," and "shRNA" are nucleic acid molecules capable of mediating RNA disturbance or genetic silencing and may inhibit the expression of a target gene to be used as an effective gene knock down method or gene therapy method. The shRNA forms a hairpin structure by binding between the complementary sequences in the single-strand oligonucleotide, and the shRNA in vivo is cleaved by a dicer to become siRNA which is a double-stranded oligonucleotide of a small RNA piece having the size of 21 to 25 nucleotides and binds specifically to mRNA with a complementary sequence to inhibit the expression. Accordingly, which means of shRNA and siRNA is used may be determined by the selection of those skilled in the art, and the shRNA and siRNA may expect a similar expression reduction effect if mRNA sequences targeting the shRNA and siRNA are the same as each other. For the purpose of the present invention, the shRNA and siRNA cleave the SYT11 mRNA molecules by specifically acting on SYT11 to induce RNA interference (RNAi), thereby inhibiting the SYT11. The siRNA may be chemically or enzymatically synthesized. The method of preparing siRNA is not particularly limited, and methods known in the art may be used. For example, the methods include a method of chemically synthesizing siRNA, a synthesis method of siRNA using in vitro transcription, a method of cleaving long double-stranded RNA synthesized by in vitro transcription using an enzyme, an expression method through intracellular delivery of an shRNA expression plasmid or viral vector, an expression method through intracellular delivery of a polymerase chain reaction (PCR)-induced siRNA expression cassette, etc., but are not limited thereto.

Specifically, the siRNA for SYT11 of the present invention may be formed of a double strand of siRNA having a nucleotide sequence selected from SEQ ID NOS: 2, 3, 4, and 5 and siRNA having a complementary sequence thereto, but is not limited thereto.

The shRNA for SYT11 of the present invention may have a nucleotide sequence selected from SEQ ID NOS: 6, 15, 16, and 17, but is not limited thereto.

For the purpose of the present invention, the antibody may be an antibody which binds to SYT11 or a ligand protein of SYT11 to inhibit the activity of SYT11.

In the present invention, the term "ligand" means a substance that forms a complex with a biomolecule to induce a biological response, and the "the ligand protein of SYT11" or "the ligand protein for SYT11" may be a protein which binds to SYT11 to activate SYT11 or increase the activity thereof.

In the present invention, the term "cancer" refers to a disease caused by overproliferation of cells. These abnormally overproliferating cells invade surrounding tissues and organs to form masses in some cases and destroy or modify the normal structure, which is called cancer. In general, the tumor refers to a mass grown abnormally by autonomous over proliferation of body tissues and may be classified into benign tumor and malignant tumor. The malignant tumor grows much faster than the benign tumor and causes metastasis while invading surrounding tissues to threaten the life. In the present invention, the cancer may be gastric cancer, lung cancer, colon cancer, rectal cancer, liver cancer, and pancreatic cancer, specifically gastric cancer. The gastric cancer is preferably a stem-like subtype and/or a mixed subtype, more preferably a stem-like subtype.

The gastric cancer may be classified according to a molecular subtype. For example, in a gastric cancer sample, mRNA expression of a full-length genetic level is examined by a microarray technique, and an intrinsic subtype in gastric cancer is confirmed through cluster analysis, and then specific genes to each subtype may be selected through statistical verification. Based on expression levels of the genes selected above, the molecular subtype may be classified into an intestinal subtype which is a subtype having high epithelial cell-characteristic gene expression, a stem-like subtype which is a subtype having high epithelial-mesenchymal transition (EMT) and stroma-derived gene expression, a mixed stromal subtype which expresses all characteristics of both the intestinal subtype and the stem-like subtype, and an inflammatory subtype which has high immune regulatory-related gene expression. It was confirmed that each subtype has a discriminatory characteristic associated with existing well-identified clinical and pathologic histological findings.

Specifically, the intestinal subtype is located mainly below the stomach and has a characteristic of good histological differentiation. On a Lauren classification, an intestinal type and an indeterminate type are frequently distributed.

On the other hand, the stem-like subtype occurs in a relatively young age group of less than 60 years of age, is located in the body and top of the stomach and has bad histological differentiation. In particular, a Signet ring cell type has a characteristic of occupying 20% of the entire tissue type, and the diffuse type on the Lauren classification is frequently distributed. In the case of the stem-like subtype, there is a clinical feature that shows a very poor prognosis.

The mixed stromal subtype shares the characteristics of the intestinal subtype and the stem-like subtype.

The inflammatory subtype is a type which is frequently located the cardia including a stomach-esophagulation joint characteristically compared with other subtypes and has poor histological differentiation. However, on the Lauren classification, there are lots of the intestinal type and the indeterminate type, and thus, the inflammatory subtype is close to the characteristic of the intestinal subtype rather than the stem-like subtype. From the prognostic aspect, the intestinal subtype and the mixed stromal subtype show a medium prognosis and the inflammatory subtype shows the best prognosis.

In the present invention, the term "metastasis" refers to a state in which the malignant tumor spreads into other tissues away from an organ occurring with the malignant tumor. As the malignant tumor starting from one organ is progressing, the malignant tumor spreads to other tissues from the organ which is a primary site occurring first, and spreading from the primary site to other tissues may be referred to as metastasis. The metastasis is a phenomenon involved in the progression of the malignant tumor and may occur while obtaining a new genetic trait as the malignant tumor cells are proliferating and the cancer is progressing. When the tumor cells obtaining the new genetic trait are invaded into blood vessels and lymphatic glands, circulated along the blood and lymph, and then fixed and proliferated in other tissues, the metastasis may occur.

Depending on a tissue where the metastasis occurs, various cancer diseases such as liver cancer, kidney cancer, lung cancer, gastric cancer, colon cancer, rectal cancer, pancreatic cancer, etc. may be caused. The composition of the present invention may prevent and treat the cancer from spreading by inhibiting the metastasis.

In the present invention, the term "inhibition" refers to all actions that inhibit the cancer metastasis with administration of the composition according to the present invention.

In the present invention, the term "subject" refers to all animals, having or developing cancer diseases of the present invention, and may be a subject excluding human beings. By administering the SYT11 inhibitor of the present invention to the subject, it is possible to exhibit an excellent effect on the treatment of cancer and inhibit metastasis to cancer.

The SYT11 inhibitor of the present invention is administered in a pharmaceutically effective dose.

In the present invention, the term "administration" means introducing the pharmaceutical composition of the present invention to a target by any suitable method, and the composition of the present invention may be administered through various oral or parenteral routes as long as the composition may reach a target tissue.

The SYT11 inhibitor may be administered to the subject appropriately in accordance with a conventional method, an administration route, and a dose, which are used in the art as intended or needed. Examples of the route of administration include oral, parenteral, subcutaneous, intraperitoneal, intrapulmonary, and intravenous routes, and the parenteral injection includes intramuscular, intravenous, intraarterial, intraperitoneal or subcutaneous routes. In addition, according to a method known in the art, a dose and the number of administration may be appropriately selected, and the dose and the number of administration of the pharmaceutical composition of the present invention to be actually administered may be appropriately determined by various factors, such as a type of symptoms, a route of administration, a gender, a health status, a dietary, age and weight of a subject, and the severity of disease.

In the present invention, the term "pharmaceutically effective dose" refers to an amount enough to inhibit or alleviate diseases at a reasonable ratio applicable to the medical use. An effective dose level may be determined according to factors including a kind of subject, the severity, age, gender, the activity of a drug, sensitivity to a drug, a time of administration, a route of administration, an excretion rate, duration of treatment, and agents to be simultaneously used, and other factors well-known in the medical field. The composition of the present invention may be administered as an individual therapeutic agent or administered in combination with other therapeutic agents, and sequentially or simultaneously administered with therapeutic agents in the related art. In addition, the pharmaceutical composition may be administered singly or multiply. It is important to administer an amount capable of obtaining a maximum effect with a minimal amount without side effects in consideration with all the factors, and the pharmaceutically effective dose may be easily determined by those skilled in the art. For example, the pharmaceutically effective dose is 0.5 to 1000 mg/day/weight kg, preferably 0.5 to 500 mg/day/weight kg.

Another aspect of the present invention for achieving the object provides a pharmaceutical composition for preventing or treating cancer comprising an expression inhibitor of Synaptotagmin 11 (SYT11) as an active ingredient.

The pharmaceutical composition of the present invention may further include suitable carriers, excipients, or diluents, which are commonly used in the preparation of the pharmaceutical composition. The composition containing a pharmaceutically acceptable carrier may have various oral or parenteral formulations. When the composition is formulated, the formulation may be prepared by using diluents or excipients, such as a filler, an extender, a binder, a wetting agent, a disintegrating agent, a surfactant, etc., which are generally used. A solid formulation for oral administration may include a tablet, a pill, a powder, a granule, a capsule, and the like, and the solid formulation may be prepared by mixing at least one excipient, for example, starch, calcium carbonate, sucrose or lactose, gelatin, and the like with at least one compound. Further, lubricants such as magnesium stearate and talc may also be used in addition to simple excipients. A liquid formulation for oral administration may correspond to a suspension, an oral liquid, an emulsion, a syrup, and the like, and may include various excipients, for example, a wetting agent, a sweetener, an aromatic agent, a preserving agent, and the like, in addition to water and liquid paraffin which are commonly used as simple diluents. A formulation for parenteral administration may include a sterile aqueous solution, a non-aqueous solution, a suspension, an emulsion, a lyophilizing agent, and a suppository. As the non-aqueous solution and the suspension, propylene glycol, polyethylene glycol, vegetable oil such as olive oil, injectable ester such as ethyl oleate, and the like may be used. As a base of the suppository, witepsol, macrogol, Tween 61, cacao butter, laurinum, glycerogelatin, and the like may be used.

Further, the pharmaceutical composition of the present invention is not limited thereto but may have any one formulation selected from the group consisting of tablets, pills, powders, granules, capsules, suspensions, oral liquids, emulsions, syrups, sterilized aqueous solutions, non-aqueous solvents, emulsions, lyophilized agents, and suppositories.

Yet another aspect of the present invention for achieving the object is to provide a use of a composition comprising a Synaptotagmin (SYT11) inhibitor in the preparation of an agent for treating cancer.

Still another aspect of the present invention for achieving the object is to provide a composition comprising a Synaptotagmin (SYT11) inhibitor to be used for treating cancer.

Still yet another object of the present invention is to provide a composition for diagnosing cancer comprising a preparation for measuring an expression level of Synaptotagmin (SYT11). For example, nucleotide sequences of SEQ ID NO: 7 and SEQ ID NO: 8 may be used as a preparation for measuring the expression level of SYT11.

Still yet another object of the present invention is to provide a method for diagnosing cancer comprising the steps of: (a) measuring an expression level of Synaptotagmin (SYT11) from an isolated biological tissue sample; (b) comparing the expression level with an expression level of SYT11 of a normal control sample; and (c) determining the cancer when the expression level of SYT11 of the isolated biological tissue sample is higher than the expression level of SYT11 of the normal control sample.

The cancer may be gastric cancer, lung cancer, colon cancer, rectal cancer, liver cancer, and pancreatic cancer, specifically gastric cancer. The gastric cancer is preferably a stem-like subtype and/or a mixed subtype, more preferably a stem-like subtype.

In the present invention, the term "diagnosis" refers to identifying the presence or characteristic of a cancer disease by measuring the presence or absence of SYT11 of the present invention in a biological tissue sample or tissue sample. In addition, a "marker or diagnosis marker" is a substance capable of diagnosing a subject with cancer cells or cancer disease separately from normal cells or a normal subject. The marker or diagnosis marker includes organic biomolecules such as polypeptides, proteins or nucleic acids (e.g., mRNA, etc.), lipids, glycolipids, glycoproteins, or saccharides (monosaccharide, disaccharide, oligosaccharide, etc.), which show an increase or decrease in cells or subjects with cancer compared to normal cells. For the purpose of the present invention, the cancer diagnosis marker of the present invention is SYT11 that is specifically expressed at an elevated level in cancer cells when compared with normal cells or tissue cells.

In the present invention, the term "isolated biological tissue sample" refers to a sample isolated from the tissue of a subject to be diagnosed, specifically gastric, lung, colon, liver and pancreatic tissues.

In the present invention, the measuring of the expression level of SYT11 may be measuring an mRNA expression level of SYT11 or a protein expression level of SYT11.

The "measuring of the mRNA expression level" is a process of confirming the presence and the expression level of mRNA of a cancer marker gene in a biological tissue sample to diagnose the cancer, which may be performed by measuring the amount of mRNA. As the analysis method for this, there are RT-PCR, competitive RT-PCR, real-time RT-PCR, RNase protection assay (RPA), Northern blotting, DNA chips, etc., but are not limited thereto.

The "measuring of the protein expression level" is a process of confirming the presence and the expression level of the protein expressed in a cancer marker gene in a biological gastric tissue sample to diagnose the cancer, and to confirm the amount of the protein by using an antibody specifically binding to the protein of the gene. As the analysis method for this, there are Western blotting, enzyme linked immunosorbent assay (ELISA), radioimmunoassay (RIA), radioimmunodiffusion, Ouchterlony immunodiffusion, rocket immunoelectrophoresis, tissue immunostaining, immunoprecipitation assay, complement fixation assay, FACS, protein chips, etc., but are not limited thereto.

As an example, the preparation for measuring the mRNA level may be a primer pair, a probe, or an anti-sense nucleotide for the mRNA of SYT11 of the present invention, and those skilled in the art may easily design a primer, probe or antisense nucleotide sequence by the polynucleotide sequence of SYT11 of the present invention. As another example, the preparation for measuring the protein level may be an antibody.

In the present invention, by confirming a possibility as the cancer diagnosis marker of SYT11, an effect capable of diagnosing the cancer was confirmed by measuring the level of SYT11.

Still yet another object of the present invention is to provide a method for screening a preparation for treating cancer comprising the steps of: (a) treating a candidate substance for treating cancer to isolated cancer cells expressing Synaptotagmin 11 (SYT11); (b) measuring an expression level of SYT11 in the isolated cancer cells treated with the candidate substance; and (c) determining the candidate substance to be used as a preparation for treating cancer when the expression level of SYT11 measured in step (b) is lower than that of isolated cancer cells non-treated with the candidate substance.

In the absence of a candidate substance capable of treating cancer, the expression level of the gene or the level of the protein encoding the gene of the present invention is measured in the cells. In addition, in the presence of the candidate substance, the expression level of the gene or the level of the protein encoding the gene of the present invention is measured, and the both expression levels are compared with each other. A substance in which the expression level of the gene or the level of the protein encoding the gene of the present invention when the candidate substance is present is reduced as compared with the level in the presence of the candidate substance may be predicted as a preparation for treating cancer.

The cancer may be gastric cancer, lung cancer, colon cancer, rectal cancer, liver cancer, and pancreatic cancer, specifically gastric cancer. The gastric cancer is preferably a stem-like subtype and/or a mixed subtype, more preferably a stem-like subtype.

The method for screening may be performed in vivo or in vitro and is not particularly limited. The candidate substance may be a known substance or a novel substance, and for example, large-scale screening may be performed through a plant extract or a chemical library. Through this, the expression or activity of SYT11 may be inhibited to discover a preparation capable of inhibiting gastric cancer, particularly stem-like subtype gastric cancer.

Hereinafter, preferred Examples and Preparation Examples will be presented in order to assist the understanding of the present invention. However, the following Examples and Preparation Examples are just provided to more easily understand the present invention, and the contents of the present invention are not limited by Examples or Preparation Examples.

<Example 1> SYT11 Expression in Stem-Like Subtype Gastric Cancer Cell Lines

Total 25 human gastric cancer cell lines were classified into four molecular subtypes by Microarray analysis: intestinal, stem-like, mixed, and inflammatory subtypes. In addition, a difference in expression of SYT11 was confirmed through western blotting and RT-PCR technique using representative 11 gastric cancer cell lines.

For a western blotting Experiment, proteins were extracted from the cell lines using a RIPA (Radio-Immuno-Precipitation Assay) lysis buffer (such as those available from MILLIPORE®), separated by polyacrylamide gel electrophoresis, and transferred to a polyvinylidene fluoride membrane and then detected using the SYT11 antibody.

The mRNAs were isolated from the cell lines using an RNA extraction solution (such as TRIZOL® from MOLECULAR RESEARCH CENTER™, INC. or INVITROGEN® from LIFE TECHNOLOGIES® CORP.) to perform RT-PCR and microarray analysis. Complementary DNA was synthesized from mRNA using RT transcript (Enzynomics). The PCR was performed using a SYT11 primer synthesized from the complementary DNA. In addition, an RPL13A primer was used as a control gene. The primer sequence information used in the experiment was shown in Table 2. After PCR, the sample was electrophoresed on an agarose gel containing ethidium bromide and irradiated with UV to identify bands.

TABLE 4

| Sequence information | Sequence |
|---|---|
| SYT11 Forward primer (SEQ ID NO: 7) | CCG GTC TCT CAG GTA ATC CT |
| SYT11 Reverse primer (SEQ ID NO: 8) | CTC ATT CTT GGT GGT GCG AT |
| RPL13A forward primer (SEQ ID NO: 9) | CAT CGT GGC TAA ACA GGT AC |
| RPL13A reverse primer (SEQ ID NO: 10) | GCA CGA CCT TGA GGG CAG C |

The microarray was performed by measuring the expression level of each gene using oligonucleotide microarray chips (such as those available from ILLUMINA™ of San Diego, Ca, USA), which were implanted with oligonucleotides capable of complementarily binding from the extracted RNA.

The result was shown in FIG. 1A and FIG. 1B.

FIG. 1A illustrates a result of microarray analysis in 25 human gastric cancer cell lines, which exhibited that the mRNA expression of SYT11 was significantly increased in the stem-like gastric cancer subtype.

FIG. 1B illustrates a result of confirming the expression of SYT11 through western blotting and RT-PCR in representative cell lines of each molecular subtype. As shown in FIG. 1B, the expression of SYT11 was greatly increased in both western blotting and RT-PCR analysis in MKN1, SK4, SNU484 and SNU638 (corresponding to cell lines having characteristics of the stem-like subtype of gastric cancer) in the stem-like gastric cancer subtype cell lines.

<Example 2> Inhibition of Migration/Invasion by SYT11 Knockdown in Gastric Cancer Cell Lines We performed experiments to determine whether siSYT11 treatment inhibits migration of gastric cancer cells using SNU484 cells among gastric cell lines. Specifically, SNU484 cells transfected with siSYT11 (SEQ ID NO: 2) and siSC (SEQ ID NO: 11) as a control were inoculated in a 96 well-Image Loc plate, grown for 24 hours, and then scratched with a wound maker. Thereafter, the migration of cells was analyzed at 0, 20, and 40 hours by wound healing assay using a real-time cell analysis system (such as the INCUCYTE® system from SATORIUS™) that enables real-time, quantitative live cell assays within a tissue culture incubator.

Figure 2:
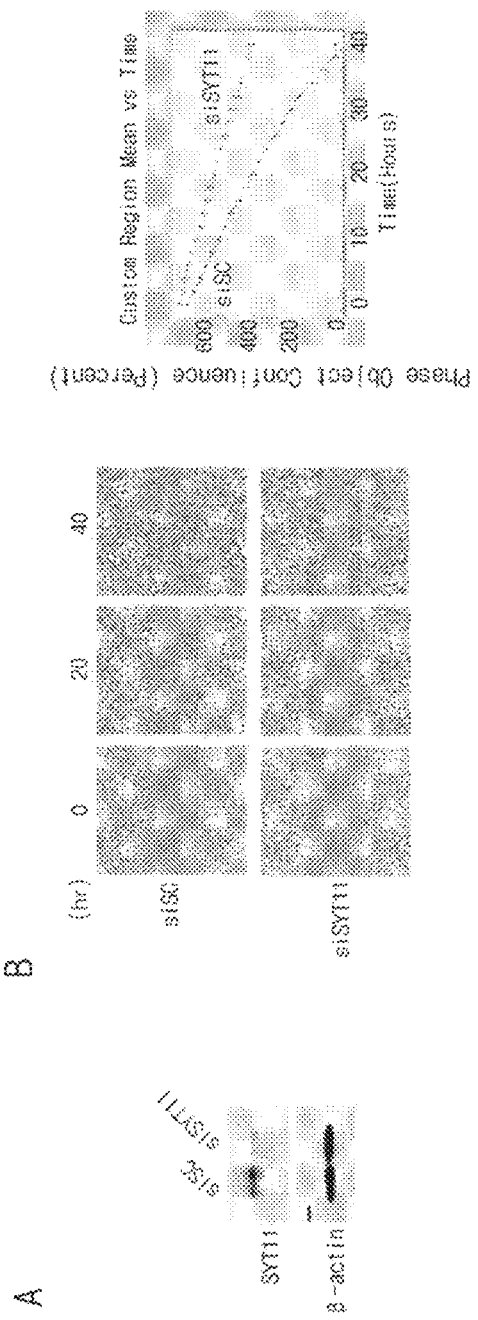
FIG. 2 is a diagram illustrating a result of confirming the inhibition of migration of a gastric cancer cell line by the reduction of SYT11 expression in the gastric cancer cell line.

The experimental result was shown in FIG. 2.

FIG. 2A illustrates the reduction of SYT11 expression by western blotting using siRNA (siSYT11) (SEQ ID NOS: 3, 4, or 5) or siSC (SEQ ID NO: 11) in SNU484 cells.

FIG. 2B is a diagram illustrating a wound healing assay result over time. As shown in FIG. 2, the migration ability of the gastric cancer cells was significantly reduced by siSYT11 treatment.

In addition, invasion assay was performed to address the inhibition of invasion by siSYT11 treatment in gastric cancer cells. Specifically, invasion assay was performed using an insert for 24-well plate cell culture. SNU484 cells transfected with siSYT11 or siSC were inoculated in an insert coated by a matrigel, and after 24 hours, the cells migrated below the insert were stained with a Sulforhodamine B (SRB) solution to measure the absorbance.

Figure 3:
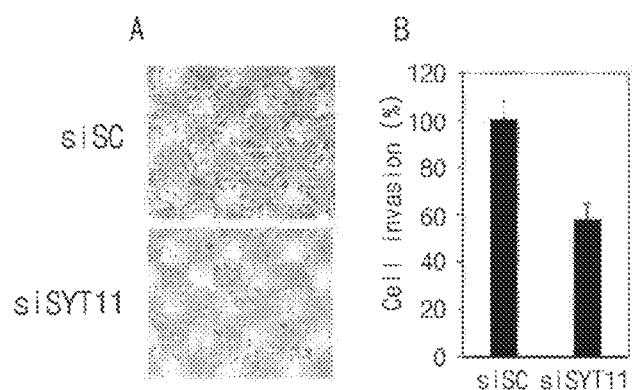
FIG. 3 is a diagram illustrating a result of confirming the inhibition of invasion of a gastric cancer cell line by the reduction of SYT11 expression in the gastric cancer cell line.

The result was shown in FIG. 3.

FIG. 3A illustrates a result of the cell invasion assay and FIG. 3B illustrates the result of quantitative analysis. As shown in FIG. 3, the SYT11 inhibition reduced about 40% of cancer cell invasion as compared with a control.

<Example 3> Confirmation of Inhibition of Ability to Adhere to Extracellular Matrix by SYT11 Knockdown in Gastric Cancer Cell Lines The extracellular matrix (ECM) provides an environment in which cells may perform a normal function as a matrix consisting of proteins and polysaccharides surrounding the outside of the cells. Integrin is present in the cell membrane and involved in the signaling related to focal adhesion through binding between cell-cell or cell-matrix, and in cancer cell metastasis process, the integrin binds to fibronectin, collagen, laminin in the extracellular matrix and function to induce cell adherence during migration of cancer cells by the binding between the cell-matrix.

Accordingly, in order to examine an effect of SYT11 on the adherence of cancer cells, SNU484 cells transfected with siSYT11 or siSC were inoculated on a 96-well plate coated with BSA, collagen, and fibronectin and washed with PBS in 1 hour to remove cells not adhering to the plate. The cells adhering to the plate were stained with an SRB solution to measure the absorbance. In addition, the SNU484 cells were transfected with siSYT11 or siSC for 48 hours. Then, changes in expression of integrin proteins were examined by performing western blotting through protein extraction and gel electrophoresis.

Figure 4:
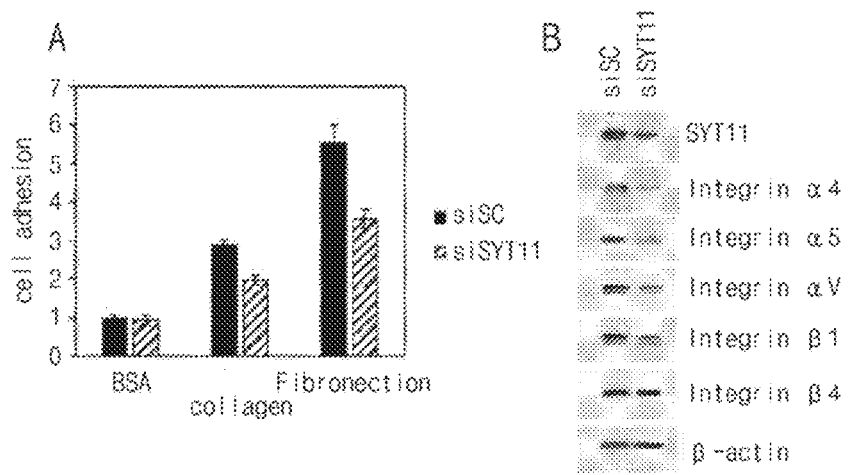
FIG. 4 is a diagram illustrating a result of confirming the inhibition of the ability to adhere to the extracellular matrix by the reduction of SYT11 expression in the gastric cancer cell line.

The result was shown in FIG. 4.

FIG. 4A illustrates an adhesion assay result. As shown in FIG. 4A, the cell binding to collagen or fibronectin was reduced by SYT11 knockdown.

FIG. 4B illustrates a result of changes in expression of integrin proteins. As shown in FIG. 4B, the expression of various integrin proteins was inhibited by SYT11 knockdown.

<Example 4> Inhibition of Secretion of Cancer Metastasis-Related Cytokines by SYT11 Knockdown in Gastric Cancer Cell Lines In order to confirm whether the SYT11 inhibition affected secretion of cancer cell metastasis-related growth factors or cytokines, cytokine array (R&D system, proteome profiler antibody arrays) was performed. Specifically, in the same manner as in Example 2, the SNU484 cells were transfected with siSYT11 or siSC and incubated for 24 hours and further incubated in the media without serum under hypoxia state (2% $O_2$) for 24 hours. Then, expression levels of cytokines of PDGF-AA, VEGF, HGF, IGFBP-2, IL-17A, IL-8, angiopoietin-1, and angiopoietin-2 in cell culture media were investigated.

In addition, cells were also collected to extract RNA and synthesize complementary DNA from mRNA using RT transcript kit (such as those available from ENZYNOM-ICS® Co. Ltd.). Thereafter, qPCR was performed using a real-time PCR premix (such as the SOLG™ PCR premixes available from SOLGENT™) with primers (such as the ACCUTARGET™ Real-Time PCR Primers from BION-EER®) VEGFA, HGF, IL-8, and Angiopoietin-1.

Figure 5:
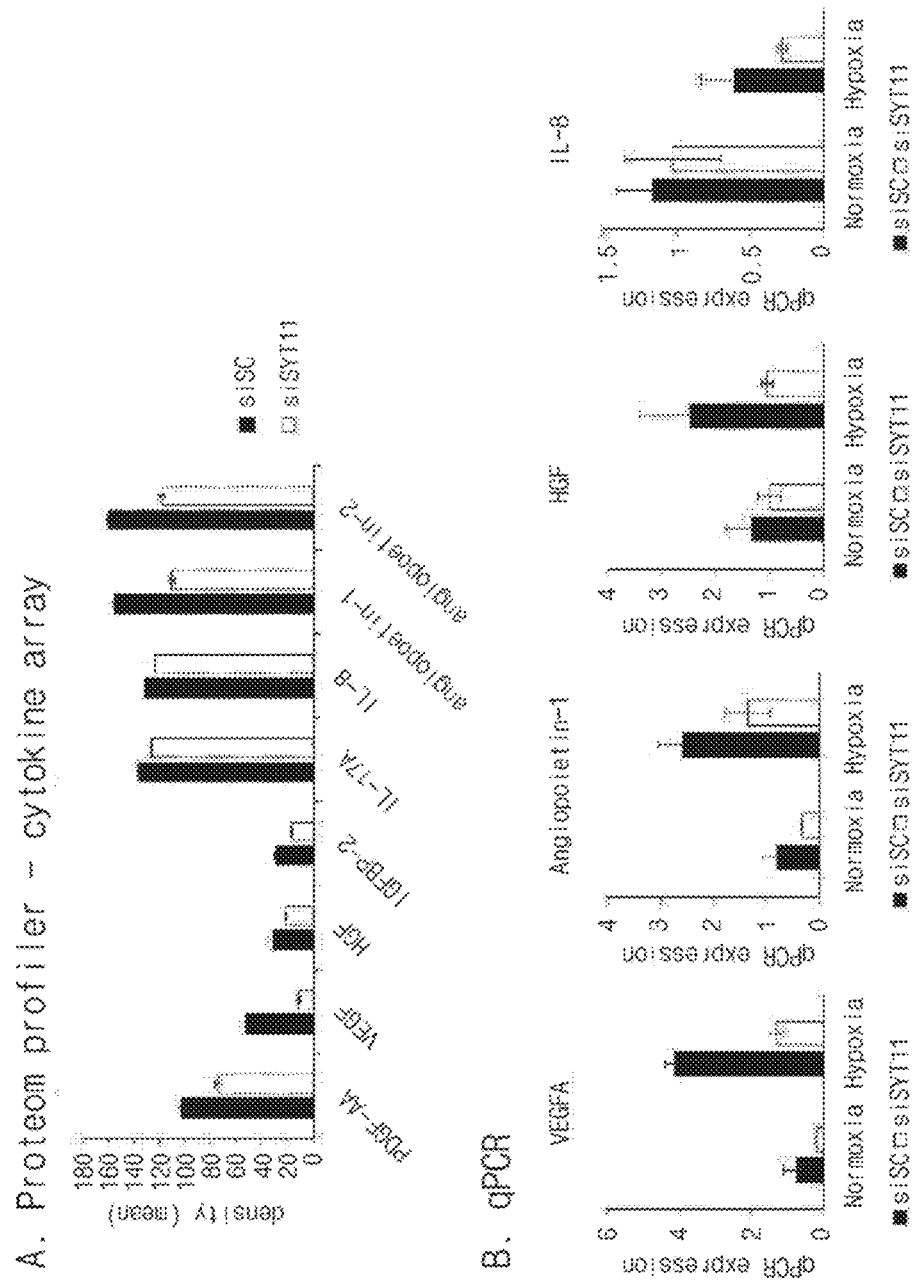
FIG. 5 is a diagram illustrating a result of confirming the inhibition of secretion of cancer metastasis-related growth factors and cytokines by the reduction of SYT11 expression in a gastric cancer cell line.

The experimental result was shown in FIG. 5.

FIG. 5A illustrates a result of performing Proteome profile-cytokine assay. As shown in FIG. 5, the secretion of the cancer cell metastasis-related growth factors or cytokines was greatly reduced by siSYT11 treatment.

In addition, FIG. 5B illustrates a result of the qPCR. As shown in FIG. 5, the mRNA expression associated with the cancer cell metastasis-related growth factors or cytokines was greatly reduced in both Normoxia and Hypoxia conditions.

<Example 5> the Effect of Cancer Treatment by SYT11 Inhibition in Animal Model

Gastric cancer cells SNU484 infected with shSYT11-Lentivirus or shControl-Lentivirus were injected to a nude mouse, and the tumor size was measured at intervals of 2 to 3 days to examine changes in mass and volume thereof.

Here, shRNA represented by shSTY11 (Sigma) has a nucleotide sequence of SEQ ID NO: 6, and shRNA represented by shControl (CTRL) (Sigma) has a nucleotide sequence of SEQ ID NO: 12.

Figure 6:
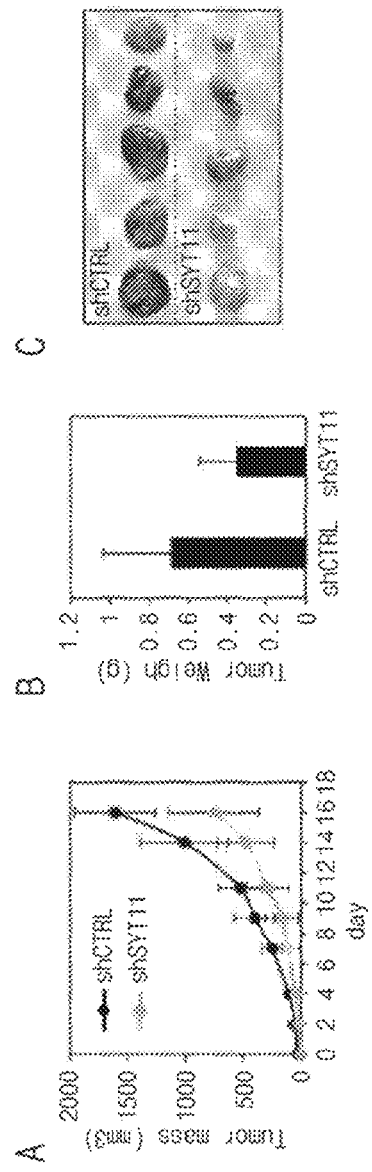
FIG. 6 is a diagram illustrating a result of confirming a tumor reduction effect according to the reduction of SYT11 expression in a mouse animal model.

The result was shown in FIG. 6. FIG. 6A illustrates a result of changes in tumor size during experiment, FIG. 6B illustrates the tumor weight after scarifying a mouse at day 16, and FIG. 6C shows the photograph of generated tumors. As shown in the results of FIG. 6, tumor formation was inhibited compared to shControl when shSYT11 was inhibited.

In addition, the tissue in animal model above was taken, and then changes in expression level of cancer cell metastasis-related growth factors or cytokines, intergrin, and a tumor-specific endothelial marker ANTXR1 were examined by qPCR in the same manner as Example 4.

At the same time, after transfection of SNU484 cells with siSYT11 or siSC, in the same manner as in Example 2, the gene expression change was examined by RT-PCR.

Figure 7:
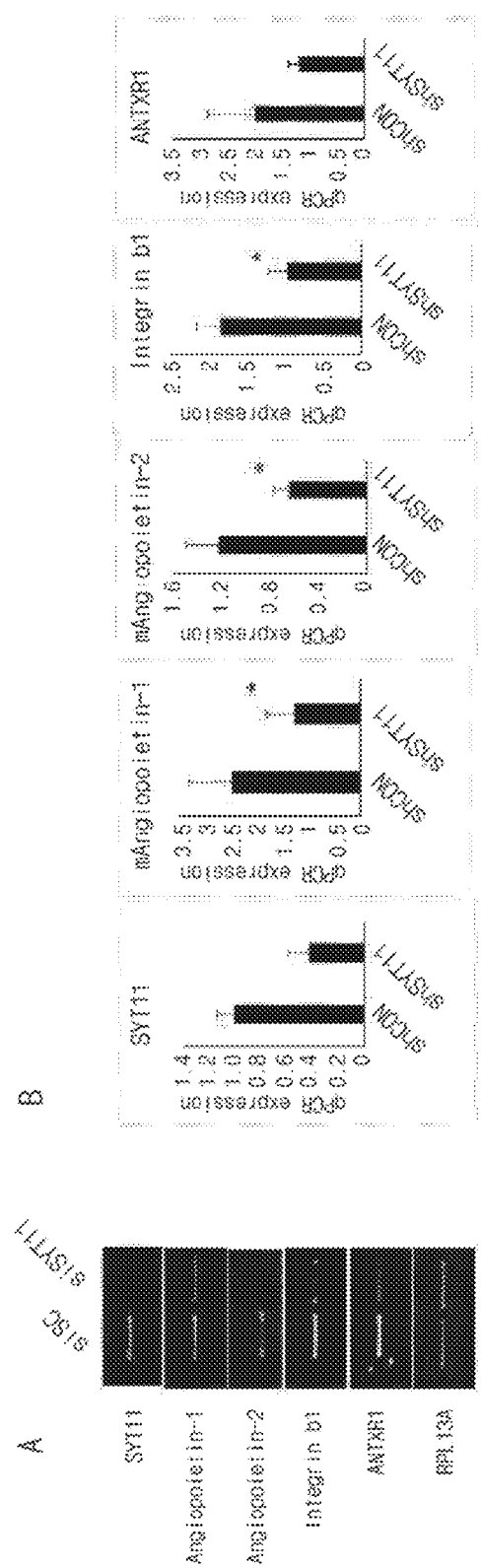
FIG. 7 is a diagram illustrating a result of confirming the inhibition of secretion of cancer metastasis-related growth factors and cytokines by the reduction of SYT11 expression in a gastric cancer cell line and a diagram illustrating a result of confirming the inhibition of secretion of cancer metastasis-related growth factors and cytokines by the inhibition of SYT11 in tumor tissues from a mouse animal model.

The result was shown in FIG. 7.

FIG. 7A demonstrated that the expression of angiopoietin-1, angiopoietin-2, intergrin-β1, and ANTXR1 was reduced in SNU484 cells by treatment of siSYT11.

As shown in FIG. 7B, the expression of angiopoietin-1, angiopoietin-2, intergrin-β1, and ANTXR1 all was reduced in an in vivo model.

<Example 6> Suppression of Cancer Cell Proliferation by SYT11 Inhibition

<6-1> Inhibition of Cancer Cell Proliferation by siRNA Treatment

SNU484 cells were transfected with siSYT11 or siSC in the same manner as in Example 2 and cell proliferation was examined for 4 days using a real-time cell analysis system.

In addition, similarly, in the same manner as in Example 2, SNU484 cells were transfected with siSYT11 (SEQ ID NOS: 2, 3, 4 or 5) or siSC and incubated for 72 hours. Then, cell viability was examined by measuring the absorbance after staining surviving cells with a sulforhodamine B (SRB) solution.

Figure 8:
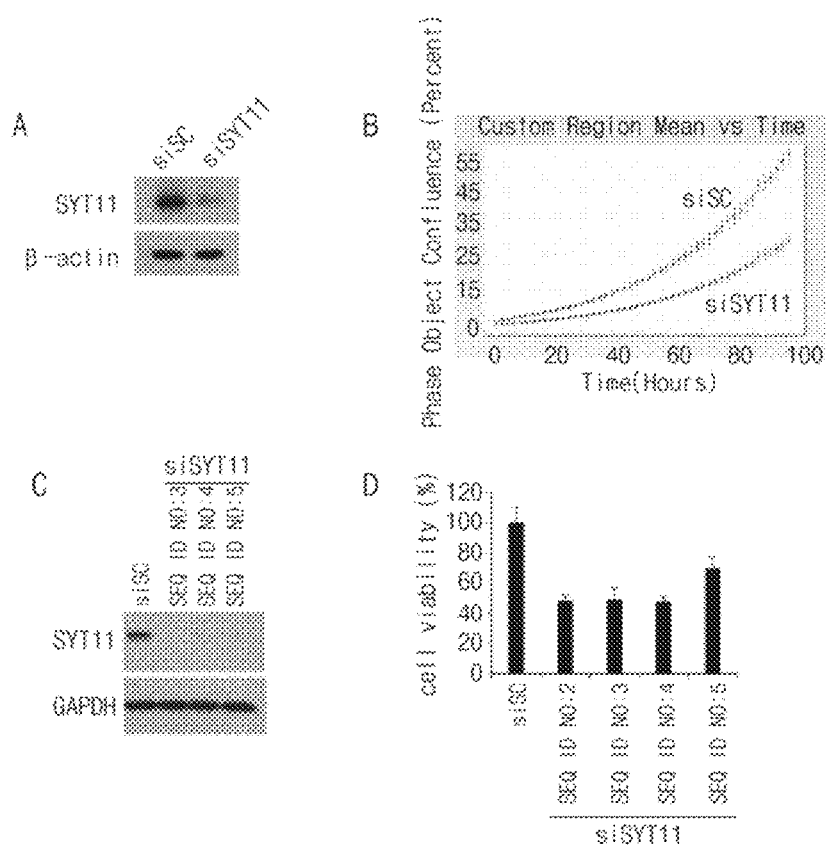
FIG. 8 is a diagram illustrating a result of confirming the inhibition of the proliferation of cells by the inhibition of SYT11 expression using various siRNAs in a gastric cancer cell line.

The result was shown in FIG. 8.

FIG. 8A illustrates reduced expression level of SYT11 by western blotting and FIG. 8B illustrates cancer cells proliferation over time.

As shown in 8A and 8B, the proliferation of cancer cells was inhibited by reducing expression of SYT11.

In addition, FIG. 8C illustrates the reduction of SYT11 expression detected by western blotting in the SNU484 cells treated with siRNA (SYT11) (SEQ ID NOS: 3, 4, or 5) or siSC (SEQ ID NO: 11), and FIG. 8D illustrates the degree of proliferation of cells treated with siRNA (SEQ ID NOS: 2, 3, 4, or 5).

<6-2> Confirmation of Inhibition of Cancer Cell Proliferation Using Antisense Oligonucleotide Like Example 6-1, SNU484 cells were transfected with antisense oligonucleotide AS-SYT11 (SEQ ID NOS: 18 or 19), or a negative control AS-NC (SEQ ID NO: 20) and the cell proliferation was examined for 3 days using a real-time cell analysis system.

At the same time, in the same manner as in Example 6-1, the SNU484 cells were treated with the antisense oligonucleotide AS-SYT11 (SEQ ID NOS: 18 or 19), or the negative control AS-NC (SEQ ID NO: 20) for 72 hours were stained with a Sulforhodamine B (SRB) solution, and then cell viability was examined by measuring the absorbance.

Figure 9:
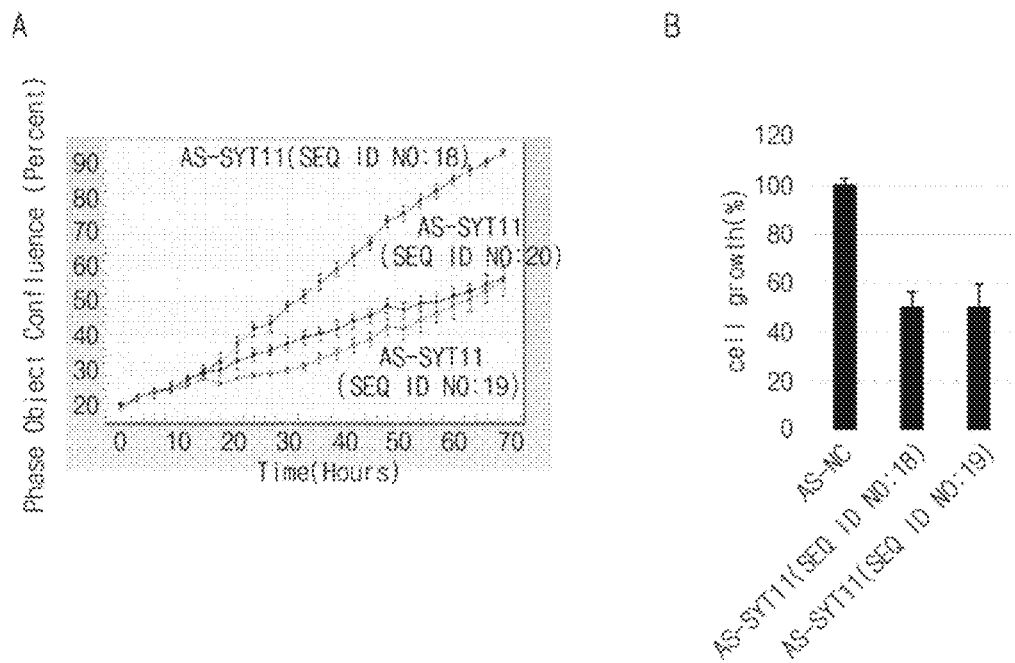
FIG. 9 is a diagram illustrating a result of confirming the inhibition of the proliferation of cancer cells using SYT11 antisense oligonucleotide in a gastric cancer cell line.

The result was shown in FIG. 9.

As shown in FIG. 9, when antisense oligonucleotides were used as an inhibitor of SYT11, like the experiment using siRNA in Examples <6-1>, the proliferation of SNU484 cancer cells was inhibited. On the other hand, when cells were treated with a negative control (SEQ ID NO: 20), the cell proliferation was not affected.

From the results, SYT11 may be used as a diagnostic biomarker of stem-like gastric cancer. In addition, inhibitor for SYT11 showed excellent effect as a composition for treating gastric cancer, by inhibiting migration and invasion of gastric cancer cells, inhibiting the ability to adhere to the extracellular matrix, inhibiting secretion of various cancer metastasis-related cytokines, and inhibiting the proliferation of gastric cancer cells.

<Example 7> SYT11-Specific Inhibition of Cancer Cell Proliferation

To examine whether knockdown of SYT4 or SYT7 affects growth inhibition of SNU484 cells. As shown in Example 2, the SNU484 cells were transfected with siSC, siSYT11, siSYT4 (SEQ ID NO: 13) inhibiting SYT4 as another gene of SYT family, or siSYT7 (SEQ ID NO: 14) inhibiting SYT7 and incubated for 72 hours. Then, cells were stained with a Sulforhodamine B (SRB) solution, and cell viability was analyzed by measuring the absorbance.

Figure 10:
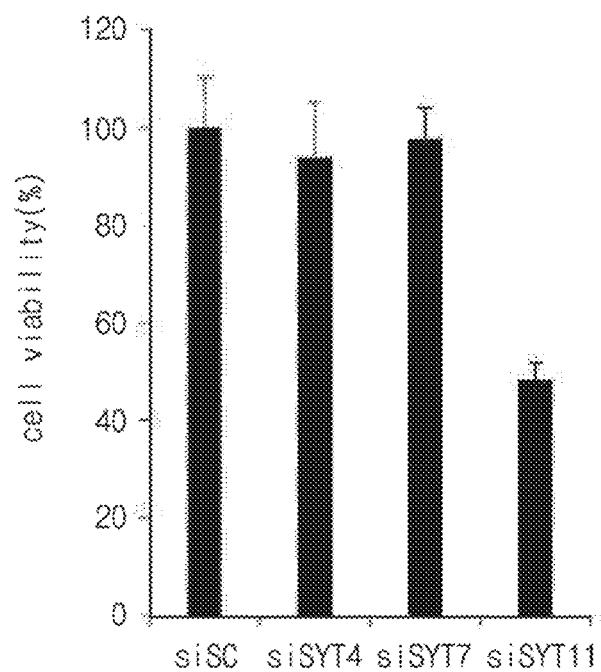
FIG. 10 is a diagram illustrating a result of comparing the cell growth inhibition according to the inhibition of expression of an SYT family in a gastric cancer cell line.

The results were shown in FIG. 10.

As shown in FIG. 10, the proliferation of SNU484 cells was selectively inhibited through SYT11 knockdown and not affected by knockdown of SYT4 or SYT7, another SYT family.

These results demonstrated that inhibition of SYT11 only may show a therapeutic effect on gastric cancer, particularly stem-like gastric cancer.

<Example 8> Inhibition of Cancer Cell Proliferation of AS-SYT11 in Various Cancer Cell Lines Gastric cancer cell lines SNU484, SNU668, and MKN1, lung cancer cell lines A549 and H1650, a colon cancer cell line HCT116, a liver cancer cell line SNU354 and pancreatic cancer cell lines ASPC1, PANC1, and MIA-PACA-2 were incubated in 96-well plates and then treated with AS-NS or AS-SYT11 next day, and cell proliferation was examined for three days by using a real-time cell analysis system.

Figure 11:
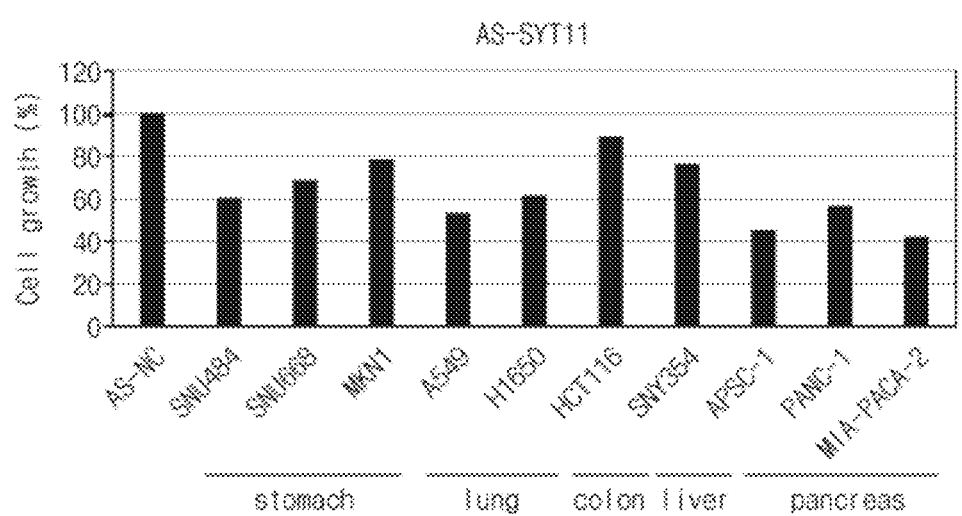
FIG. 11 is a diagram illustrating an effect of inhibiting the proliferation of cancer cells by SYT11 antisense oligonucleotide in various cancer cell lines.

The result was shown in FIG. 11.

As confirmed in FIG. 11, when the growth of cells treated with AS-NC was calculated as 100%, the effect of inhibition on gastric cancer, lung cancer, liver cancer, and pancreatic cancer cells by the AS-NC treatment was evaluated.

From the above result, it can be seen that the inhibitor of SYT11 has a treatment effect even in lung cancer, colon cancer, liver cancer, and pancreatic cancer as well as gastric cancer.

<Example 9> Effect of AS-SYT11 on the Inhibition of Tumor Formation in Animal Model A gastric cancer cell line MKN1 ($1 \times 10^7$ cells) was injected into a nude mouse for tumor formation. After a week, AS-NC and As-SYT11 were administered into a tumor site by 5 mg/kg 3 times a week. The volume of the tumor was measured three times/week for three weeks. After the end of the experiment, the weight of tumor extracted thereof was measured.

Figure 12:
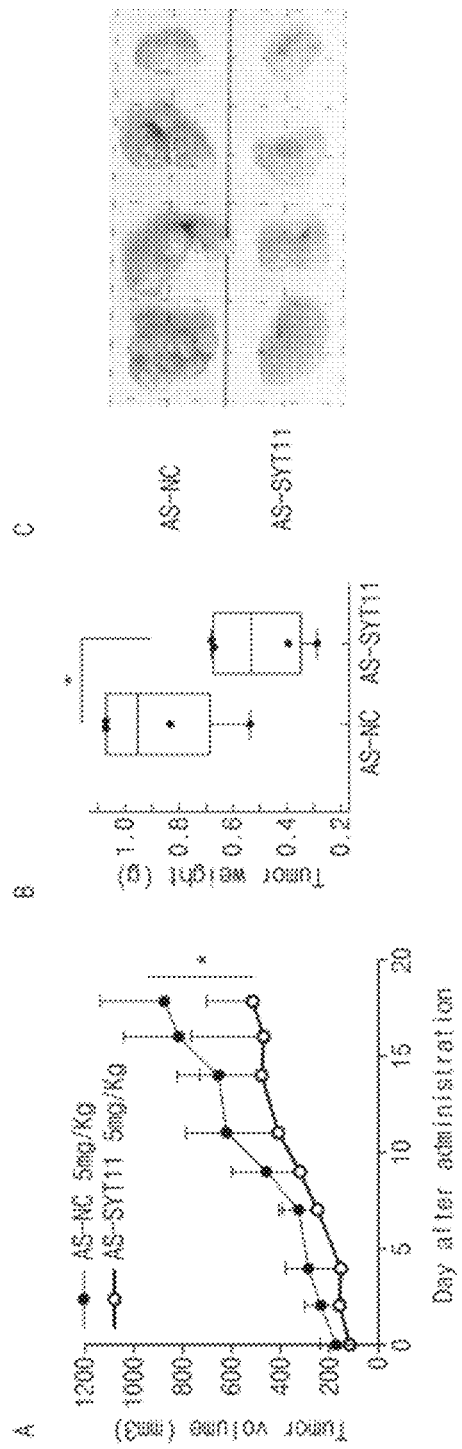
FIG. 12 is a diagram illustrating an effect of inhibiting the tumor formation by SYT11 antisense oligonucleotide in a mouse animal model.

The result was shown in FIG. 12. FIG. 12A illustrates a result of changes in tumor size according to a date, FIG. 12B illustrates a result of the weight of tumor, and FIG. 12C shows a photograph of the generated tumor.

As confirmed in FIG. 12, it was shown that groups administered with AS-SYT11 suppressed the volume and weight of tumors as compared to groups administered with AS-NC.

From the above result, it can be seen that AS-SYT11, the inhibitor of SYT11 also has a gastric cancer treatment effect in vivo model.

The invention claimed is:

1. A method for treating a gastric cancer in a subject, comprising administering a Synaptotagmin 11 (SYT11) nucleic acid inhibitor to the subject,
   wherein the SYT11 inhibitor is selected from a group consisting of: siRNA, shRNA and an antisense oligonucleotide; and
   wherein the siRNA and shRNA inhibit expression of the SYT11 mRNA, and the antisense oligonucleotide reduces the expression of the SYT 11 protein.

2. The method of claim 1, wherein the siRNA has a nucleotide sequence selected from the group consisting of SEQ ID NO: 2, SEQ ID NO: 3, SEQ ID NO: 4 and SEQ ID NO: 5.

3. The method of claim 1, wherein the shRNA has a nucleotide sequence selected from the group consisting of SEQ ID NO: 6, SEQ ID NO: 15, SEQ ID NO: 16 and SEQ ID NO: 17.

4. The method of claim 1, wherein the antisense nucleotide has a nucleotide sequence selected from the group consisting of SEQ ID NO: 18 and SEQ ID NO: 19.

5. The method of claim 1, wherein the gastric cancer is gastric cancer having a stem-like or mixed subtype.

* * * * *